(12) United States Patent
Saadat (10) Patent No.: US 6,277,115 B1
(45) Date of Patent: Aug. 21, 2001

(54) APPARATUS AND METHOD FOR TREATING BODY TISSUES

(75) Inventor: Vahid Saadat, Redwood Shores, CA (US)

(73) Assignee: Ethicon, Inc., New Brunswick, NJ (US)

(*) Notice: Subject to any disclaimer, the term of this patent is extended or adjusted under 35 U.S.C. 154(b) by 0 days.

(21) Appl. No.: 09/455,114

(22) Filed: Dec. 6, 1999

Related U.S. Application Data (63) Continuation of application No. 08/905,188, filed on Aug. 4, 1997, now abandoned.

(51) Int. Cl.$^7$ ............................................. A61B 15/18
(52) U.S. Cl. ............................. 606/41; 606/46; 606/48; 606/50
(58) Field of Search ................................ 600/372, 373; 606/41–50; 607/101, 102, 156, 119, 122; 128/898

(56) References Cited

U.S. PATENT DOCUMENTS

| | | |
|---|---|---|
| 4,682,596 | 7/1987 | Bales et al. . |
| 5,458,597 | 10/1995 | Edwards et al. . |
| 5,584,872 | 12/1996 | LaFontaine et al. . |
| 5,607,462 | 3/1997 | Imran . |
| 5,643,197 | 7/1997 | Brucker et al. . |
| 5,676,693 | 10/1997 | LaFontaine . |
| 5,800,482 * | 9/1998 | Pomeranz et al. ............... 607/101 |
| 6,076,012 * | 6/2000 | Swanson et al. .................. 604/21 |
| 6,099,526 * | 8/2000 | Whayne et al. ................... 606/41 |

FOREIGN PATENT DOCUMENTS

| | | |
|---|---|---|
| 95 34346 A | 12/1995 | (WO) . |
| WO95/34346 A1 | 12/1995 | (WO) . |
| 96 07360 A | 3/1996 | (WO) . |
| WO96/07360 A1 | 3/1996 | (WO) . |
| 97 15238 A | 1/1997 | (WO) . |
| WO97/00646 A1 | 1/1997 | (WO) . |
| 97 18765 A | 5/1997 | (WO) . |
| WO97/15238 A1 | 5/1997 | (WO) . |
| WO97/18765 A1 | 5/1997 | (WO) . |
| 97 00646 A | 9/1997 | (WO) . |

* cited by examiner

*Primary Examiner*—Linda C. M. Dvorak
*Assistant Examiner*—David M. Ruddy
(74) *Attorney, Agent, or Firm*—Verne E. Kreger, Jr.

(57) ABSTRACT

An apparatus, system, and method for treating body tissue includes an electrode assembly having a first electrode and a second electrode, with at least the first electrode formed of porous conductive material, such as porous metal. Conductive fluid is delivered to the operating site through the porous metal of the first electrode via a fluid supply conduit. The apparatus may also include a fluid withdrawal conduit. The second electrode may also be formed of porous metal, and may serve as the intake opening for the fluid withdrawal conduit. The electrode assembly may be positioned on a catheter shaft having a distal end, with the first electrode positioned on the catheter shaft distal end. In treating desired tissue at a selected operational site, the electrode assembly is introduced to the site with the first electrode positioned adjacent to the desired tissue. Conductive fluid, such as a saline solution, is delivered to the operational site via the supply conduit. Electrical power is provided across the first electrode and second electrode via a power supply, which may be an RF power supply.

6 Claims, 7 Drawing Sheets

APPARATUS AND METHOD FOR TREATING BODY TISSUES

CROSS REFERENCE TO RELATED APPLICATION

This application is a continuation of U.S. application Ser. No. 08/905,188, filed on Aug. 4, 1997, now abandoned.

BACKGROUND OF THE INVENTION

1. Field of the Invention

The invention relates to a device for treatment of body tissues. More particularly, the present invention relates to an apparatus and method for treatment, including vaporization and coagulation, of body tissues using an electrode comprising a porous metal in conjunction with a conductive fluid such as saline.

2. Description of Related Art

Electrosurgery has been used for treating body tissue, including coagulation, desiccation, and vaporization of tissue. A common method of performing electrosurgery involves injecting conductive fluid, such as saline solution, into the operational site. The conductive fluid serves to create an electrical path between the electrodes and the body tissue.

Continuous replenishment of the conductive fluid can be important during various procedures. The fluid can be absorbed by the patient's body. Furthermore, fluid may become contaminated, thus compromising its conductivity and/or other desirable characteristics, such as clarity.

When sufficient power is applied across the electrodes, the electrodes can become heated and may vaporize all fluid in immediate contact with the electrodes. The electrode may the heat up to a point where they are damaged.

To maintain a constant supply of conductive fluid at the operational site, fluid can be continuously introduced to the operational site. However, delivering the fluid to the area immediately adjacent the electrode, without adversely interfering with the electrode function, can be critical to system performance.

Consequently, there is a need to efficiently introduce fluid to an operational site, and specifically over the electrosurgical electrodes, without adversely impacting the function of the electrodes. The present invention satisfies these needs.

SUMMARY OF THE INVENTION

Briefly and in general terms, the present invention provides an electrosurgical instrument and system for treating tissue at a selected operation site, including a first electrode comprising porous conductive material, such as sintered metal, and a first electrical lead in electrical connection with the first electrode. The instrument may further include a fluid supply conduit in fluid communication with the porous metal of the first electrode, wherein fluid may be supplied to the operation site via the porous metal and fluid supply conduit. A fluid withdrawal conduit may be used to withdraw fluid from the operational site.

A second electrode may be positioned on the instrument. The second electrode may be formed of porous metal, forming the opening for a fluid withdrawal conduit through which fluid is extracted from the operational site.

The instrument may be part of an electrosurgical system including a power supply for generating a voltage between the first electrode and the second electrode. The system may further include a fluid source providing fluid to the operational site via the fluid supply conduit. A controller may be used to monitor and control the power supply, fluid source, and fluid withdrawal.

During a surgical procedure, the first electrode is positioned adjacent the tissue to be treated. Conductive fluid is introduced to the operational site by injecting fluid from a supply conduit through the porous metal of the first electrode. Electrical power is provided to the first electrode to effect the desired treatment.

Other features and advantages of the present invention will become more apparent from the following detailed description of the invention when taken in conjunction with the accompanying drawings.

DETAILED DESCRIPTION OF THE PREFERRED EMBODIMENTS

The present invention is depicted in FIGS. 1 through 6 for use in treating body tissues, including use in treating a human uterus. However, the present invention is not limited to use in the female reproductive system, and may be applied to various electrosurgical procedures.

Figure 1:
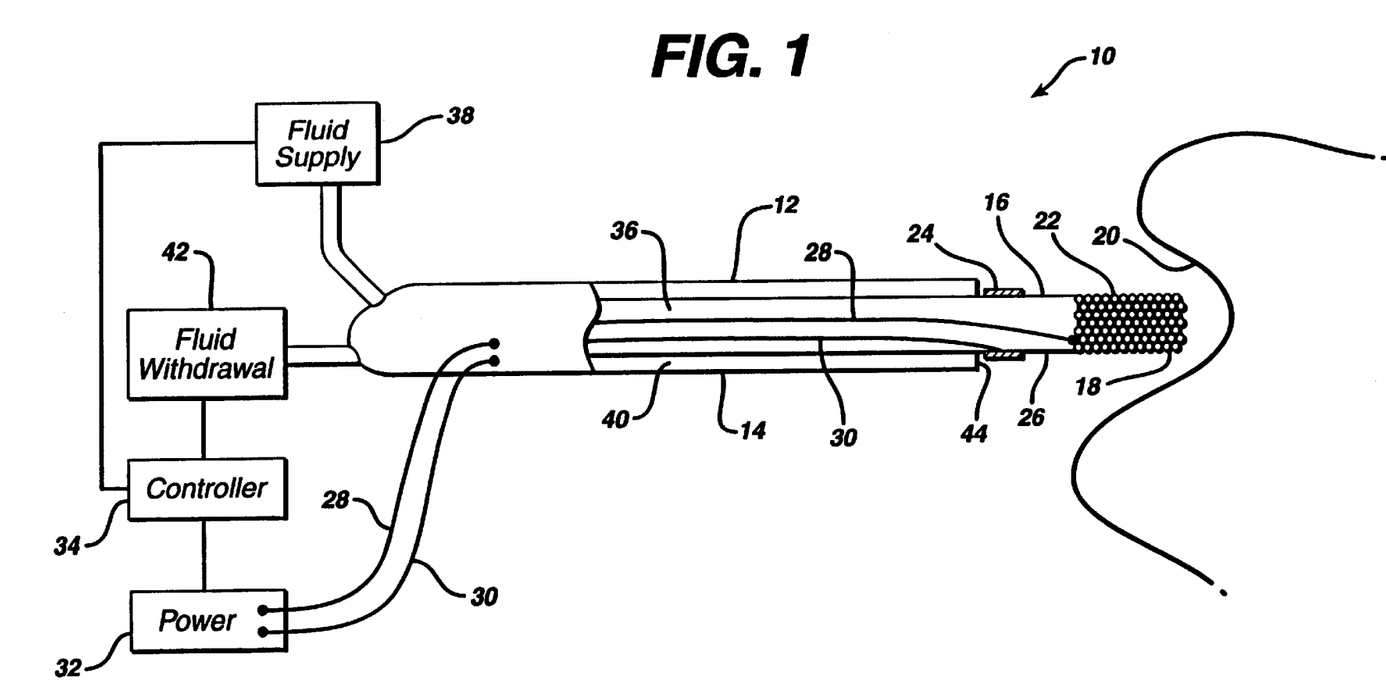
FIG. 1 is a side view, in partial cross section, of a system according to one embodiment of the present invention.
Figure 1A:
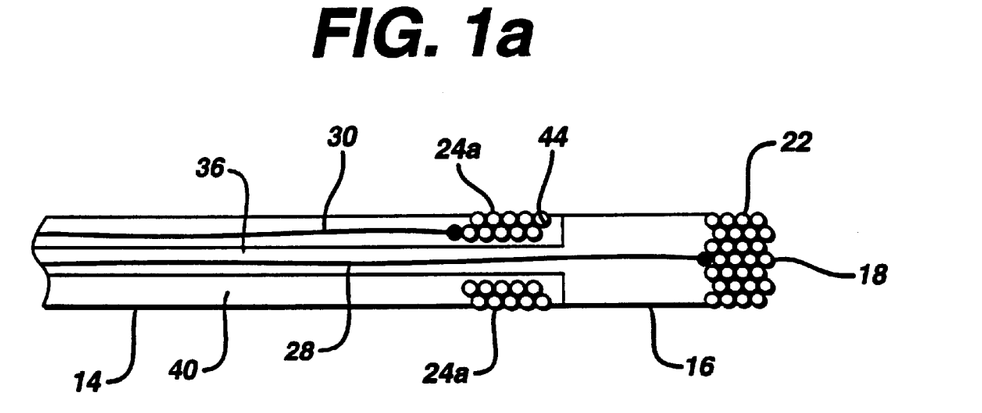
FIG. 1a is a side view, in cross section, of an electrosurgical instrument according to another embodiment of the present invention.

Referring now to FIG. 1, in one preferred embodiment the system 10 of the invention comprises an electrosurgical instrument 12 including a generally elongated shaft 14 having an electrode assembly 16 at the shaft distal end 18. The electrode assembly is shown positioned at a desired operational site 20. The electrode assembly 16 includes a first electrode 22 formed of sintered metal.

A sintered metal structure is typically made by placing a metal powder or a collection of very small metal spheres (such as BB pellets) in an oven. By increasing the temperature in the oven to the point where the surface of the pellets reach the softening point, but not quite the melting point, adjacent spheres will fuse together at their points of contact, thereby becoming sintered. The voids between the spheres preferably remain open, thereby forming a generally-open cell foam-like structure. Because the spheres did not entirely melt, they did not coalesce into a single and generally solid mass. The resulting structure is a porous metal structure with a plurality of small passageways.

An alternative to sintered metal is to form multiple holes, such as by drilling, in a metal structure, thereby forming a porous metal structure. For example, multiple holes could be drilled into a section of tubing, thereby creating multiple passageways for fluid to flow out of and/or into the tubing.

The electrode assembly 16 may include a second electrode 24 positioned on the shaft 14. The second electrode 24 and the first electrode 22 are preferably insulted from each other. For example, in the embodiment of FIG. 1, the catheter shaft 14 is formed of a generally non-conductive material. The catheter shaft portion 26 between the first electrode 22 and the second electrode 24 thus serves as an insulator.

The first electrode 22 and second electrode 24 are electrically connected, via a first electrical lead 28 and a second electrical lead 30, respectively, to a power supply 32 that generates a voltage between the first electrode 22 and second electrode 24. In the embodiment shown, a controller 34 monitors and controls the output power according to pre-programmed instructions and/or input from the surgeon or other user.

In the embodiment of FIG. 1, the first electrode 22 is positioned at the distal end 18 of the catheter shaft 14. A fluid supply conduit 36 within the catheter shaft leads to the first electrode 22, so that fluid introduced to the fluid supply conduit 36 from a fluid supply 38 will flow out of the porous metal of the first electrode 22, thereby introducing the fluid to the operational site 20. The fluid is preferably a conductive fluid.

A fluid withdrawal conduit 40 may be provided through which may be withdrawn from the operational site 20 by a fluid withdrawal device, such as the fluid withdrawal pump 42 shown in FIG. 1. The fluid withdrawal conduit 40 is shown with an intake opening 44 positioned on the catheter shaft 14 proximally of the first electrode 22.

Alternate positions of the intake opening are within the scope of the invention. For example, in the embodiment shown in FIG. 1a, the second electrode 24a is formed of porous metal. The second electrode 24a is positioned over the intake opening 44, so that fluid is withdrawn through the porous metal of the second electrode 24a.

Referring again to FIG. 1, the controller 34 may monitor and control the fluid supply 38 and, in the event of a malfunction of either the fluid supply 38 or the power supply 32, operate to shut down operation. For example, the controller 34 may automatically shut off the power supply 32 if the fluid supply 38 is no longer providing fluid to the operational site 20.

Figure 2:
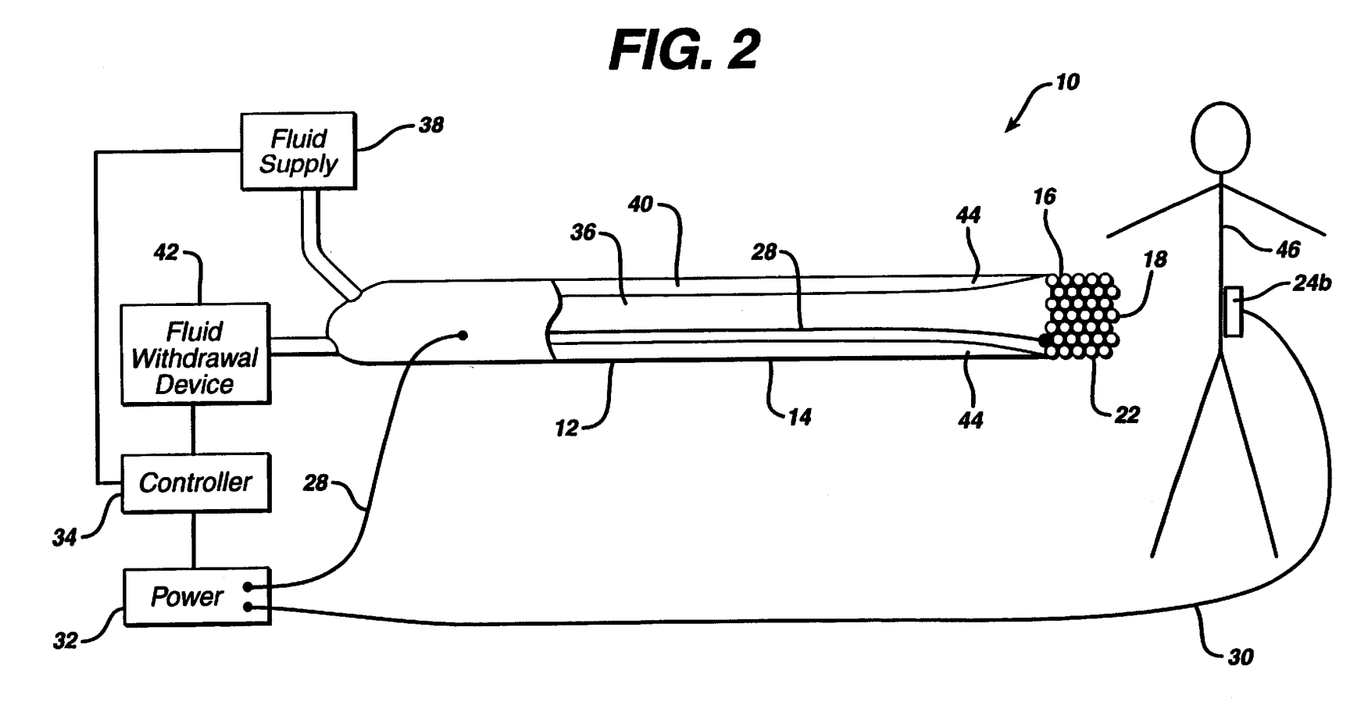
FIG. 2 is a side view, in partial cross section, of a system according to a further embodiment of the present invention.

In the embodiment shown in FIG. 1, the electrode assembly 16 is a bipolar electrode assembly, including a first electrode 22 and a second electrode 24. The invention, however, is also applicable to monopolar electrode assemblies, as shown in FIG. 2. In FIG. 2, the second electrode 24b is a grounding pad which may be positioned in electrical contact with the patient's body. In such an embodiment, the patient's body 46 serves as the electrical connection between the first electrode 22 and the second electrode 24b.

Figure 3:
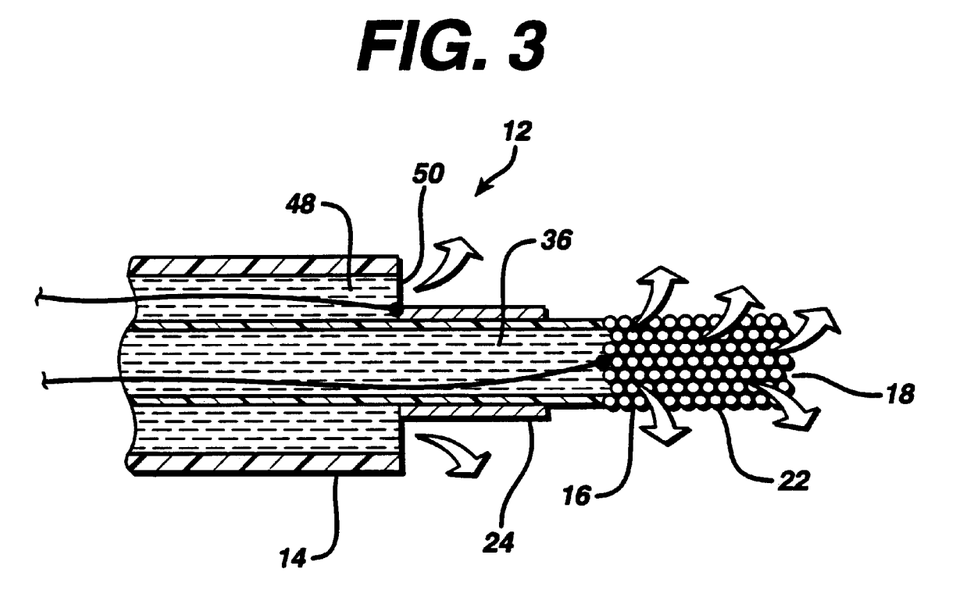
FIG. 3 is a side view, in partial cross section, of an electrosurgical instrument according to an embodiment of the invention.

FIG. 3 shows an electrosurgical instrument 12 according to one embodiment of the invention. The electrode assembly 16 is positioned at the distal end 18 of a catheter shaft 14. The electrode assembly includes a first electrode 22 formed of sintered metal, and a second electrode 24 positioned proximally of the first electrode 22. A fluid supply conduit 36 runs through the center of the catheter shaft 14 and discharges conductive fluid through the porous metal of the first electrode 22.

A second fluid conduit 48 runs through the shaft 14 and has a fluid opening 50 positioned proximally of the second electrode 24. The second fluid conduit 48 may be used as an additional fluid supply conduit to infuse additional fluid. Alternatively, the second fluid conduit 48 may be used as a fluid withdrawal conduit to remove excess fluid from an operational site.

Figures 4, 4A:
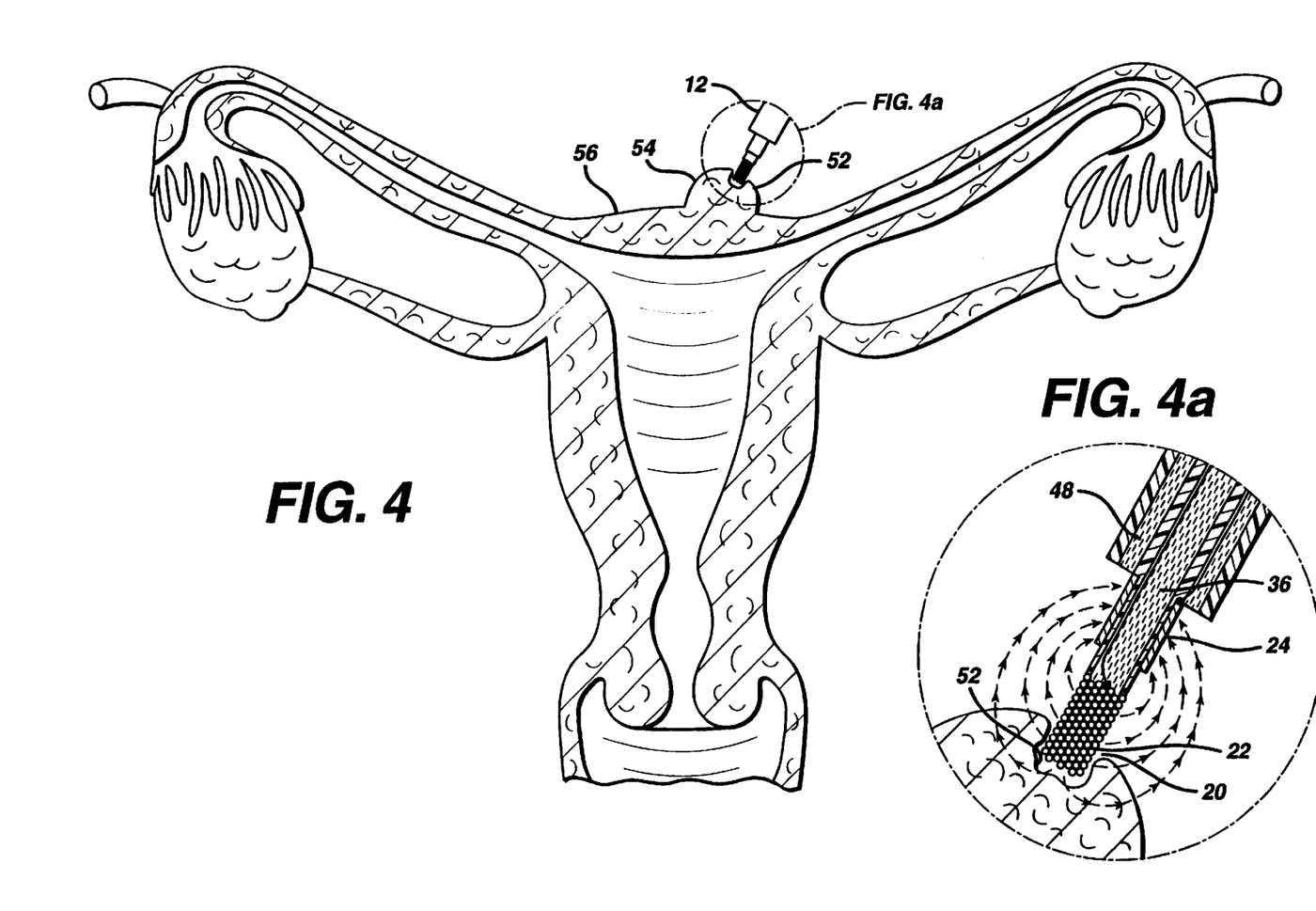
FIG. 4 is a side view, in partial cross section, of showing the electrosurgical instrument of FIG. 3 during a surgical procedure.
FIG. 4a is close up side view, in partial cross section, showing details of FIG. 4.

FIG. 4 shows the electrosurgical instrument 12 of FIG. 3 used to remove selected tissue 52, such as a cyst 54, on an outer portion of a human uterus 56. As shown in greater detail in FIG. 4a, the first electrode 22 is positioned adjacent the selected tissue 52, with the second electrode 24 not being in direct contact with the tissue 52. Power is applied between the first electrode 22 and second electrode 24, thereby inducing a desired effect on the selected tissue 52. In the procedure shown in FIG. 4, the desired effect is tissue vaporization. Conductive fluid is introduced to the operation site via the fluid supply conduit 36, which introduces the fluid through the porous metal of the first electrode 22. The conductive fluid creates an electrical pathway from the first electrode 22 and the second fluid electrode 24. The conductive fluid may be withdrawn from the operational site 20 during the procedure via the second fluid conduit 48. Fluid withdrawal may occur simultaneously with fluid introduction, thereby continuously replenishing the fluid at the operational site 20.

FIG. 4 depicts the electrosurgical instrument being used for tissue vaporization, whereby the first electrode is placed adjacent the desired tissue, power is applied to vaporize the tissue, and then the instrument is advanced further into the tissue as the overlaying tissue is vaporized. The electrosurgical instrument may also be used to desiccate and ablate tissue, which may involve moving the first electrode across the tissue surface in a side-to-side movement.

Figure 5:
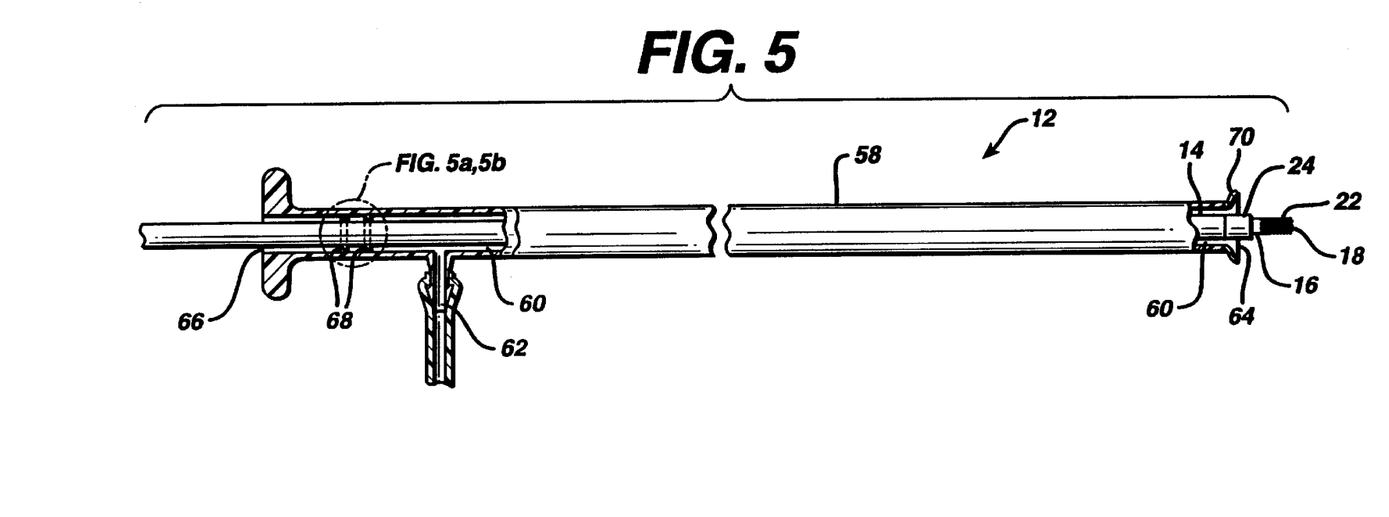
FIG. 5 is a side view, in partial cross section, of an electrosurgical instrument according to a further embodiment of the invention.
Figure 5A:
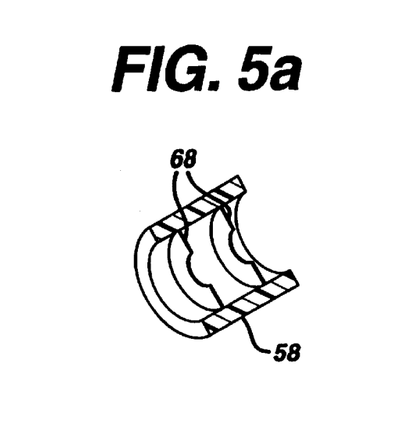
FIG. 5a is close up side view, in partial cross section, showing details of FIG. 5.
Figure 5B:
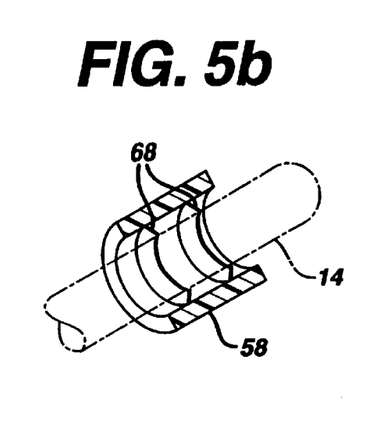
FIG. 5b is close up side view, in partial cross section, showing details of FIG. 5.
Figures 6, 6A:
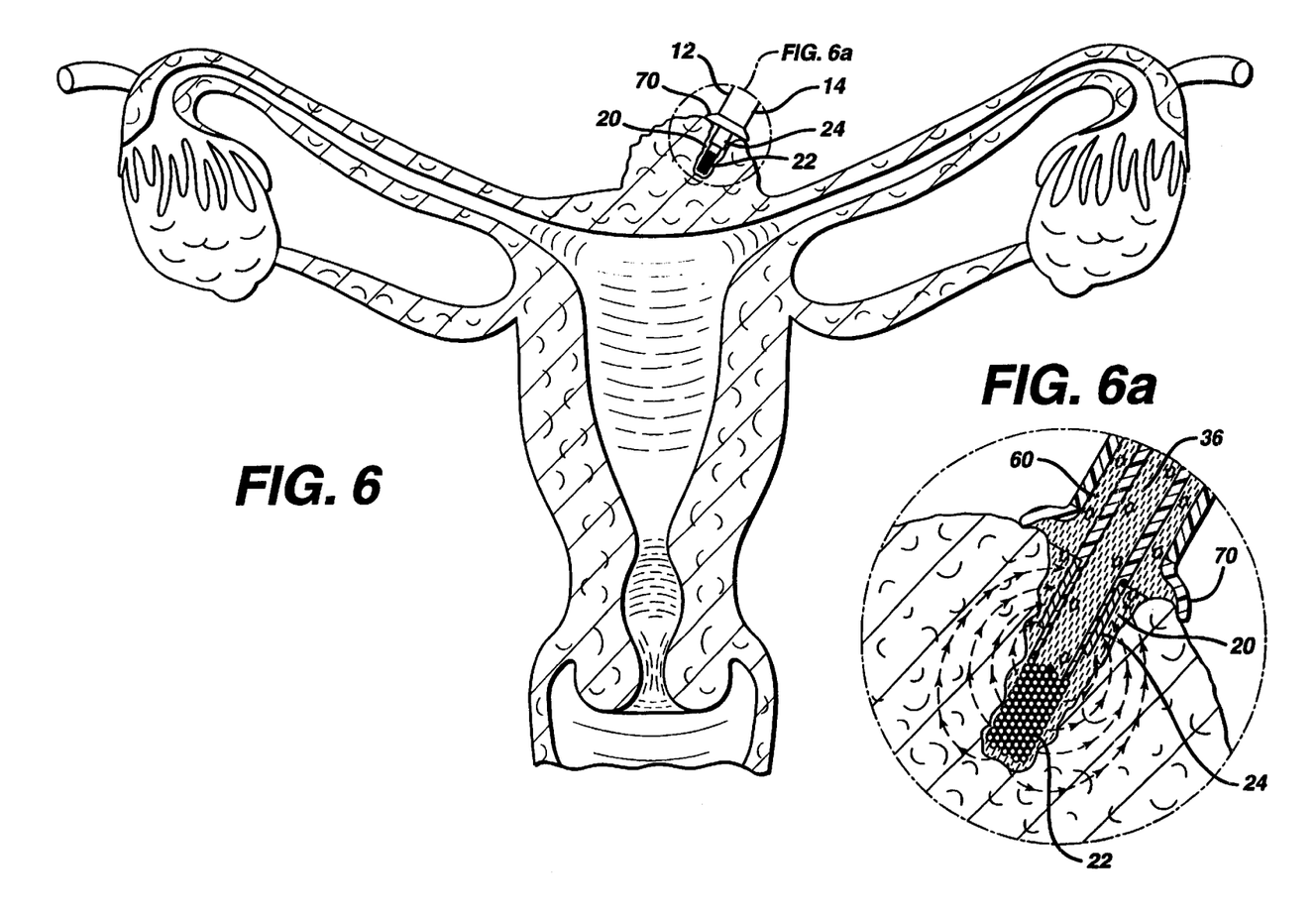
FIG. 6 is a side view, in partial cross section, showing the electrosurgical instrument of FIG. 5 during a surgical procedure.

FIG. 5 shows a further embodiment of an electrosurgical instrument 12 according to the invention, including a sheath 58 that surrounds the catheter shaft 14. The sheath 58 forms an outer conduit 60 surrounding the catheter shaft 14. The sheath 58 may include a fluid withdrawal outlet 62, that can be used to withdraw fluid from an operational site via the outer conduit 60.

The sheath 58 may be slidably positioned about the catheter shaft 14 so that the electrode assembly 16 can be advanced out of and pulled back into the distal opening 64 of the sheath 58. The sheath 58 may be configured to allow the catheter shaft 14 to be entirely removed from the sheath 58. The sheath 58 may further be configured so that the catheter shaft 14, and the particularly the shaft distal end 18 and electrode assembly 16, can be removed from side to side within the sheath 58.

To prevent fluid from leaking out of the proximal end 66 of the sheath 58, one or more membrane valves 68 are positioned within the sheath 58. As shown in greater detail in FIGS. 5a and 5b, which show the membrane valves 68 before (FIG. 5a) and after (FIG. 5b) insertion of the catheter shaft 14, the membrane valves 68 may be configured to slidably receive the catheter shaft 14 and form a seal thereabout to prevent fluid leakage, even during movement of the shaft 14 within the sheath 58.

The sheath 58 may include a flared extension 70 about the sheath distal opening 64. As shown in greater detail in FIG. 6, the flared extension 70 serves to trap conductive fluid at the operational site 20, thereby creating a pocket of conductive fluid. As power is applied to the first electrode 22 and second electrode 24, conductive fluid is introduced to the operational site 20 via the fluid supply conduit 36 and porous metal of the first electrode 22, and withdrawn from the site via the outer conduit 60.

Although, preferred and alternative embodiments of the invention have been described and illustrated, the invention is susceptible to modifications and adaptations within the ability of those skilled in the art and without the exercise of inventive faculty. Thus, it should be understood that various changes in form, detail, and usage of the present invention may be made without departing from the spirit and scope of the invention. Accordingly, it is not intended that the invention be limited, except as by the appended claims.

What is claimed is:

1. A method of treating selected tissue using an electrode assembly, the method comprising the steps of:

(a) providing an electrosurgical instrument having an electrode assembly including a first electrode and a second electrode, wherein the first electrode comprises porous conductive material;

(b) introducing the electrode assembly into a selected operation site;

(c) placing the first electrode adjacent the selected tissue and maintaining the second electrode out of contact with the tissue;

(d) surrounding the electrode assembly with a conductive fluid so that the conductive fluid defines an electrical path between the first electrode and the selected tissue and the second electrode; and (e) applying sufficient output power to the electrode assembly to induce a desired treatment on the selected tissue.

2. The method of claim 1, wherein the electrosurgical instrument further includes a fluid delivery conduit in fluid communication with the porous conductive material of the first electrode, and step (d) includes delivery conductive fluid through the fluid delivery conduit to the porous conductive material of the active electrode.

3. The method claim 1, wherein step (c) includes the further step of:

(f) moving the active electrode across a surface of the tissue.

4. The method of claim 3, wherein step (f) includes moving the electrode across the tissue surface in a side-to-side motion.

5. The method of claim 1, wherein the conductive fluid comprises a saline solution.

6. The method of claim 1, wherein the first electrode comprises porous conductive metal.

\* \* \* \* \*

UNITED STATES PATENT AND TRADEMARK OFFICE
CERTIFICATE OF CORRECTION

PATENT NO. : 6,277,115 B1  
DATED : August 21, 2001  
INVENTOR(S) : Vahid Saadat It is certified that error appears in the above-identified patent and that said Letters Patent is hereby corrected as shown below:

<u>Column 6,</u>
Line 12, change "delivery" to -- delivering --

Signed and Sealed this

Tenth Day of June, 2003

JAMES E. ROGAN
*Director of the United States Patent and Trademark Office*